(12) United States Patent
Restaino

(10) Patent No.: US 6,764,832 B2
(45) Date of Patent: Jul. 20, 2004

(54) **PLATING MEDIA FOR THE PRESUMPTIVE IDENTIFICATION OF THE GENUS SHIGELLA AND THE SPECIES *SHIGELLA SONNEI* AND *SHIGELLA BOYDII***

(76) Inventor: Lawrence Restaino, 43 W. 513 Tall Oaks Trail, Elburn, IL (US) 60119

( * ) Notice: Subject to any disclaimer, the term of this patent is extended or adjusted under 35 U.S.C. 154(b) by 68 days.

(21) Appl. No.: 09/934,506

(22) Filed: Aug. 22, 2001

(65) Prior Publication Data

US 2003/0049718 A1 Mar. 13, 2003

(51) Int. Cl.$^7$ .............................. C12Q 1/04; C12Q 1/06; C12Q 1/08; C12Q 1/02; G01N 33/53

(52) U.S. Cl. .......................... 435/34; 435/968; 435/39; 435/38; 435/40; 435/29; 435/973

(58) Field of Search .......................... 435/34, 968, 39, 435/38, 40, 29, 973

(56) References Cited

U.S. PATENT DOCUMENTS 3,870,601 A * 3/1975 Warren et al. ................ 435/12
5,726,031 A * 3/1998 Roth et al. .................... 435/34
6,350,588 B1 * 2/2002 Roth et al. .................... 435/34

* cited by examiner

Primary Examiner—Louise N. Leary
(74) Attorney, Agent, or Firm—Marshall A. Burmeister

(57) ABSTRACT

A solid growth plating medium in which Shigella organisms will grow and form colonies in the medium, and substantially, other microorganisms are inhibited or their colonies are differentiated from Shigella organisms. In one embodiment of the invention, colonies produced by Shigella appear with the color of the plating medium, usually a clear off-white color, that can be readily observed. In another embodiment, the fact that *Shigella boydii* and *Shigella sonnei* produce the enzyme alpha-galactosidase, but most *Shigella dysenteriae* and *Shigella flexneri* strains do not, is utilized with a chromogenic substrate to produce colonies of these microorganisms of a distinguishing color.

23 Claims, No Drawings

PLATING MEDIA FOR THE PRESUMPTIVE IDENTIFICATION OF THE GENUS SHIGELLA AND THE SPECIES *SHIGELLA SONNEI* AND *SHIGELLA BOYDII*

The present invention relates to the presumptive identification of bacteria, and in particular to the presumptive identification of Shigella. The genus Shigella is classified in the family Enterobacteriaceae, and has four species, namely, *Shigella dysenteriae*, *Shigella flexneri*, *Shigella boydii* and *Shigella sonnei*. One embodiment of the present invention relates to plating media for identifying the genus Shigella, and a second embodiment of the present invention relates to plating media for simultaneously identifying *Shigella boydii* and *Shigella sonnei*.

BACKGROUND OF THE INVENTION

Shigella organisms produce ulcerative colon infections in humans called shigellosis or bacillary dysentery. The organisms are transmitted directly or through food or water contaminated with fecal matter. In order to combat the spread of shigellosis, public health professionals and health care professionals require a means for rapidly and quantitatively identifying the presence of Shigella organisms in samples containing a plurality of other organisms. Shigella is generally found in mixed samples containing organisms of other Enterobacteriaceae.

Scientists have long searched for an effective means for isolating, detecting and identifying Shigella organisms. In 1987, the *Journal of Food Protection* (Smith, J. L., Shigella as a *Foodbourne Pathogen*, volume 50, page 788) reviewed methods used for the isolation and detection of Shigella from suspect foods. Nonetheless, plating media developed prior to the present invention produce excessive false negative and false positive organism counts, and were difficult to read.

The biochemical characteristics of Shigella, and its similarity to *Escherichia coli*, significantly increase the likelihood of false negative and false positive indications from a plating medium. Table I hereafter, published in the *Compendium of Methods for the Microbiological Examination of Foods*, Edited by Carl Vanderzant and Don F. Splittstoesser, 1992, American Public Health Association, page 429, makes it clear that Shigella does not have characteristics that are readily identified in a plating medium.

TABLE 1

Selected Biochemical Characteristics of the Genus Shigella for Speciation

| Medium | Reaction |
| --- | --- |
| KCN broth | negative |
| malonate broth | negative |
| tryptone broth (indole) | positive or negative (*S. dysenteriae* 1, *S. flexneri* 6 and *S. sonnei* are negative; *S. dysenteriae* 2 is positive) |
| MR-VP medium | positive methyl red negative Voges-Proskauer |
| citrate agar | negative |
| decarboxylase medium | |
| with lysine | negative |
| with ornithine | negative |
| acetate differential agar | negative (some strains of *S. flexneri* 4a are positive) |

TABLE 1-continued

Selected Biochemical Characteristics of the Genus Shigella for Speciation

| Medium | Reaction |
| --- | --- |
| indicator broth | |
| with glucose | acid (some strains of *S. flexneri* 6 and *S. boydii* 13 and 14 produce acid and gas) |
| with adonitol, xylose, cellobiose, dulcitol, inositol, salicin | no acid (*S. boydii* is variable on xylose) |
| with lactose | no acid (some strains of *S. flexneri* 2a and *S. boydii* 9 produce acid, *S. sonnei* produces acid after several days) |
| with sucrose | no acid (*S. sonnei* produces acid after several days) |
| with mannitol | acid (*S. dysenteriae* does not produce acid; some strains of S. flexncri 4a and 6 do not produce acid) |
| with raffinose | no acid (*S. flexneri* is variable; *S. sonnei* produces acid after several days) |

From Table 1 it is clear that the different strains of Shigella do not react to conventional media in the same way, and that false positives and false negatives are likely to occur. Paragraph 26.24 of the *Compendium of Methods for the Microbiological Examination of Foods*, supra, recommends the use of three media of different selectivity to assay a single sample in order to increase the accuracy of the media, which makes for a costly and cumbersome isolation procedure.

Further, Shigella organisms do not react to many biochemical tests. They do not utilize KCN, malonate, citrate, or acetate as sole carbon sources. They produce acid from glucose and mannitol* but do not produce acid from sorbitol, adonitol, dulcitol, inositol, xylose*, cellobiose, lactose*, sucrose*, raffinose*, or salicin. Shigellae generally do not produce gas from sugar* (*see Table 1).

The 1999 U.S. Pat. No. 5,871,944 of Russel G. Miller and Edward Mallinson entitled *Salmonellae Preferential Media* discloses a plating medium for identification of Salmonella and Shigella from a mixed bacterial sample with ingredients for preferential growth of these bacteria and a chromogenic substrate that reacts to the enzyme beta-galactosidase to differentiate other bacteria. Other bacteria that do not produce beta-galactosidase will not be differentiated from Salmonella or Shigella, resulting in false positives.

SUMMARY OF THE INVENTION

It is an object of the present invention to provide a novel plating medium for isolating and quantitatively identifying Shigella organisms from a sample containing a plurality of different organisms; and a further object of the invention to provide a plating medium for making a combined identification of *Shigella boydii* and *Shigella sonnei* organisms from a mixed sample.

It is also an object of this invention to provide such plating media for the isolation and identification of Shigella organisms that will produce fewer false positive and fewer false negative identifications than the plating media of the prior art.

Further, it is an object of this invention to provide such a plating medium for the isolation and identification of Shigella organisms from a mixed sample that will produce a more readily readable plate with colonies of fewer colors than the plating media of the prior art to facilitate identification of Shigella organisms.

For many public health and health care professionals, *Shigella boydii* and *Shigella sonnei* are the strains of Shigella of greatest interest. It is therefore a further object of the present invention to provide a plating medium for the combined isolation and quantitative identification of *Shigella boydii* and *Shigella sonnei* organisms.

The objects of the invention are accomplished by providing a solid growth plating medium in which Shigella organisms will grow and form colonies in the medium. Substantially, other microorganisms are inhibited or their colonies are differentiated from Shigella organisms, i.e. transformed to a color distinguishing the Shigella colonies. Differentiation is accomplished by providing in that medium a plurality of biochemical ingredients that produce reactions with the other organisms of the sample to color the colonies of the other organisms a minimum of colors that contrast with the color of the Shigella colonies. In one embodiment of the invention, colonies produced by Shigella appear with the color of the plating medium, usually a clear off-white color, that can be readily observed. In another embodiment, the fact that *Shigella boydii* and *Shigella sonnei* produce the enzyme alpha-galactosidase, but most *Shigella dysenteriae* and *Shigella flexneri* strains do not, is utilized with a chromogenic substrate to produce colonies of these microorganisms of a distinguishing color.

The invention will be more readily understood from the following detailed description, which contains no drawings.

DETAILED DESCRIPTION

Mixed samples containing Shigellae often contain other bacteria of the Enterobacteriaceae and other bacteria. In both embodiments of the present invention, Shigellae form colonies in the plating medium of a particular color, and the other bacteria are subjected to reactions changing the color of these colonies to a different color.

Before differentiation of the bacteria can occur, an inoculated plate is incubated to produce bacterial growth. Nutrients are provided in the plating medium to facilitate growth of Shigella, and the inventor has found casamino acids, dessicated beef extract, yeast extract, sodium pyruvate and soytone to be desirable nutrients. Agar functions to thicken the mixture, and it is used in sufficient quantity to solidify the mixture. Carbohydrates are also incorporated in the plating medium to provide for growth. The inventor has found carbohydrates of the group lactose, sucrose, salicin, 2-deoxy-D-ribose, adonitol, dulcitol, inositol, xylose and cellobiose to be particularly satisfactory.

Some organisms can be prevented from colonizing the plating medium by incorporating inhibitors in the medium. If it is likely that they will be present in the sample, it is desirable to inhibit as many unwanted organisms as can reasonable be inhibited. One group of organisms that my readily be inhibited are gram-positive bacteria which are inhibited by bile salt #3 and other forms of bile salts. Other inhibitors that may be used in the media of this invention are tellurite to retard the growth of *Escherichia coli*, sodium novobiocin and cefixime to inhibit Proteus sp. and cefsulodin to suppress pseudomonas-like bacteria.

The plating media of the present invention differentiate the colonies of the microorganisms that cannot be inhibited from the Shigella colonies by use of a pH indicator dye and one or more chromogenic substrates. The chromogenic substrates react to an enzyme and produce a water insoluble precipitate of a particular color, and the precipitate is maintained in the region of the colony that produced it to color that colony with the color of the precipitate. Different chromogenic substrates react with different enzymes, but they can be selected to produce precipitate of essentially the same color. Hence, colonies of different bacteria, that react with different substrates, will produce colonies colored by precipitate of the same color, thus reducing the number of colors that the observer must note in order to count the plate.

The inventor has found that the following chromogenic and fluorogenic substrates may be used in the media of the present invention: 5-Bromo-4-chloro-3-indoxyl-alpha-D-galactopyranoside, 6-chloro-3-indoxyl-alpha-D-galactopyranoside, 4-Methylumbelliferyl-alpha-D-galactopyranoside, 1-Naphthyl-alpha-D-galactopyranoside, 4-Nitrophenyl-alpha-D-galactopyranoside, 4-Methylumbelliferyl-alpha-D-glucopyranoside, 2-Naphthyl-alpha-D-glucopyranoside, 4-Nitrophenyl-alpha-D-glucopyranoside, 5-Bromo-4-chloro-3-indoxyl-alpha-D-glucopyranoside, 5-Bromo-4-chloro-3-indoxyl-beta-D-glucopyranoside, 5-Bromo-6-chloro-3-indoxyl-beta-D-glucopyranoside, 3-indoxyl-beta-D-glucopyranoside, 6-chloro-3-indoxyl-beta-D-glucopyranoside, 5-Bromo-4-chloro-3-indoxyl-alpha-D-mannopyranoside, 2-(6-Bromonaphthyl)-alpha-D-mannopyranoside, 6-chloro-3-indoxyl-alpha-D-mannopyranoside, 4-Methylumbelliferyl-alpha-D-mannopyranoside, 4-Nitrophenyl-alpha-D-mannopyranoside, 4-Methylumbelliferyl-beta-D-mannopyranoside, 4-Nitrophenyl-beta-D-mannopyranoside, Methylumbelliferyl-beta-D-xylopyranoside, 2-Nitrophenyl-beta-D-xylopyranoside, 4-Nitrophenyl-beta-D-xylopyranoside, 5-Bromo-4-chloro-3-indoxyl-beta-D-fucopyranoside, 4-Methylumbelliferyl-beta-D-fucopyranoside, 4-Nitrophenyl-beta-D-fuicopyranoside, 4-Methylumbelliferyl-beta-D-glucopyranoside, 1-Naphthyl-beta-D-glucopyranoside, 2-Nitrophenyl-beta-D-glucopyranoside, 3-Nitrophenyl-beta-D-glucopyranoside, 4-Nitrophenyl-beta-D-glucopyranoside, 5-Bromo-4-chloro-3-indoxyl-N-acetyl-beta-D-galactosaminide, 6-chloro-3-indoxyl-N-acetyl-beta-D-galactosaminide, 4-Methylumbelliferyl-N-acetyl-beta-D-galctosaminide, and 4-Nitrophenyl-N-acetyl-beta-D-galactosaminide.

The response of a chromogenic substrate to an enzyme may be inadequate to produce precipitate to fully color its colony. It is therefor desirable to add an enhancer to the medium to increase the production of precipitate. The inventor has found the following enhancers to be effective with the chromogenic substrates set forth above: 1-O-Methyl-alpha-D-galactopyranoside, 1-O-Methyl-beta-D-glucopyranoside, and 1-O-Methyl-alpha-D-mannopyranoside.

Table 2 sets forth the ingredients of one particular plating medium according to the present invention. This plating medium is exemplary of one embodiment of the present invention, and will identify Shigella. All four strains of Shigella will form colonies in the plating medium of the color of the medium, an off-white solid.

TABLE 2

Ingredients For General Shigella Medium

| INGREDIENTS | GRAMS/LITER |
| --- | --- |
| Casamino acids | 14.37 |
| 13eef extract, dessicated | 1.0 |
| Yeast extract | 6.0 |
| Lactose | 8.0 |
| Soytone | 5.0 |
| Sodium chloride | 5.0 |

TABLE 2-continued

Ingredients For General Shigella Medium

| INGREDIENTS | GRAMS/LITER |
|---|---|
| Bile salts #3 | 0.6 |
| Bile salts | 0.2 |
| Sucrose | 8.0 |
| Dulcitol | 8.0 |
| 5-Bromo-4-chloro-3-indoxyl-beta-D-glucopyranoside | 0.2 |
| 1-O-Methyl-beta-D-glucopyranoside | 0.15 |
| 5-Bromo-4-chloro-3-indoxyl-beta-D-fucopyranoside | 0.2 |
| 5-Bromo-4-chloro-3-indoxyl-N-Acetyl-beta-D-galactosaminide | 0.2 |
| Phenol red | 0.08 |
| Agar | 15.0 |
| Novobiocin | 0.002 |
| Cefsulodin | 0.006 |

The ingredients, except for the last two, are mixed in any order, the pH is adjusted to 6.6 to 6.8, the ingredients are boiled to dissolve the agar, and the mixture is permitted to cool to room temperature. Thereafter, novobiocin and cefsulodin are added under sterile conditions. The composition is then poured into plates and permitted to dry for 48 to 72 hours, and it is then ready to be used. Storage time of poured plates is as much as 90 days at 2 to 8 degrees Celsius.

Table 3 sets forth data taken with a batch of plating media containing the ingredients set forth in Table 2 from a mixed sample containing the named bacterial strains.

TABLE 3

| Organism | Colonial Morphology |
|---|---|
| Shigella sonnei (3 strains) | White to clear raised; 2–3 mm in diameter |
| Shlgella boydii | White to clear raised; 1 mm in diameter |
| Shlgella flexneri | White to clear raised; 2 mm in diameter |
| Shigella dysenteriae | White to clear raised; 2 mm in diameter |
| Escherichia coli | Yellow raised |
| Escherichia coli | Yellow-green raised |
| Klebseilla pneumoniae | Green raised |
| Enterobacter aerogenes | Green raised |
| E. coli 01 57:H7 | Yellow raised |
| Salmonella derby | Yellow raised |
| Salmonella duesseldorf | Yellow raised |

In some locations, Shigella boydii and Shigella sonnei have proven to be of particular interest to public health officials and health care workers. A second embodiment of the present invention set forth in Table 4 is effective in making a combination identification of Shigella sonnei and Shigella boydii from a mixed bacterial sample. Shigella sonnei and Shigella boydii produce the enzyme alpha-galactosidase, but most Shigella dysenteria and Shigella flexneri strains do not. The plating medium of Table 4 contains a substrate that is responsive to alpha-galactosidase, and hence produces a precipitate of a color to identify these strains of Shigella.

TABLE 4

Ingredients for Shigella sonnei and Shigella boydii Medium

| INGREDIENTS | GRAMS/LITER |
|---|---|
| Casamino acids | 14.5 |
| Soytone | 5.0 |
| 13eef extract, dessicated | 1.0 |
| Yeast extract | 6.12 |
| Sodium chloride | 5.0 |
| Lactose | 8.0 |
| Sucrose | 8.0 |
| Salicin | 8.0 |
| Dulcitol | 8.0 |
| Bile salts #3 | 0.6 |
| 5-Bromo-4-chloro-3-indoxyl-alpha-D-galactopyranoside | 0.2 |
| 1-O-Methyl-alpha-D-galactopyranoside | 0.2 |
| Bile salts | 0.2 |
| Phenol red | 0.08 |
| Agar | 15.0 |
| Novobiocin | 0.002 |
| Cefsulodin | 0.006 |
| Cefixime | 0.00005 |

This medium may be prepared in the same manner as the medium of Table 2. In this medium, the chromogenic substrate, 5-Bromo-4-chloro-3-indoxyl-alpha-D-galactopyranoside, reacts with Shigella sonnei and Shigella boydii to add precipitate to these colonies, and to function as a differentiator with respect to most Shigella flexneri and Shigella dysenteriae. Accordingly, most Shigella flexneri and Shigella dysenteriae strains produce clear colonies in the medium, as shown in Table 5 which reports the test results produced by inoculating the medium of Table 4 with essentially the same sample used to produce the test results of Table 3.

TABLE 5

| Organism | Colonial Morphology |
|---|---|
| Shigella sonnei | Blue center with clear ring; 2–3 mm in diameter |
| Shigella boydii | Blue colony raised; 1 mm in diameter |
| Shigella flexneri | Clear, raised colony, 2 mm. in diameter |
| Shigella dysenteriae | Clear, raised colony, 2 mm. in diameter |
| Escherichia coli | Yellow raised |
| Escherichia coli | Yellow-green raised |
| Klebseilla pneumoniae | Yellow raised |
| Enterobacter aerogenes | Yellow raised |
| E. coli 0157:H7 | Yellow green raised |
| Salmonella derby | Yellow green raised |
| Salmonella duesseldorf Enteroinvasive | Yellow green raised |
| Escherichia coli | Blue center with clear ring 1–3 mm. in diameter |

The foregoing test results indicate that plating media according to the first embodiment of the present invention are capable of identifying Shigella bacteria from a mixed bacterial sample with accuracy, and further indicate that plating media according to the second embodiment of the present invention are capable of identifying combined Shigella sonnei and Shigella boydii from a mixed bacterial sample.

In the first embodiment, a pH indicator dye (phenol red) and a plurality of chromogenic substrates (5-Bromo-4-chloro-3-indoxyl-beta-D-glucopyranoside, 5-Bromo-4- chloro-3-indoxyl-beta-D-fucopyranoside, and 5-Bromo-4-chloro-3-indoxyl-N-acetyl-beta-D-galactosaminide) are used to differentiate the colonies of Shigella from the colonies of other bacteria. Shigella does not produce enzymes that will react with the chromogenic substrates or acid to excite the pH indicator dye, and therefore clear Shigella colonies are formed on the surface of the medium. Those other bacteria that produce acid will cause the indicator dye to color these colonies with the color of the dye, namely yellow. Those other bacteria that produce an enzyme that reacts with any one or more of the chromogenic substrates will release precipitate into its colonies of the color of the substrate, namely dark blue, since all of the substrates release precipitate of this same dark blue color. Those other bacteria that produce acid and an enzyme that will react with one or more of the chromogenic substrates, will inject into its colonies both the dye of the pH indicator and the precipitate of the substrate, and the yellow dye will mix with the dark blue precipitate to color these colonies a shade of green.

In the second embodiment, a pH indicator dye (phenol red) and one chromogenic substrates (5-Bromo-4-chloro-3-indoxyl-alpha-D-galactopyranoside) are used to differentiate the colonies of *Shigella sonnei* and *Shigella boydii* from the colonies of other bacteria. *Shigella sonnei* and *Shigella boydii* produce the enzyme alpha-galactosidase, and this enzyme reacts with the chromogenic substrate 5-Bromo-4-chloro-3-indoxyl-alpha-D-galactopyranoside to release dark blue precipitate into its colonies. With some exceptions, other bacteria that produce the alpha-galactosidase enzyme, and hence release dark blue precipitate into its colonies, also produce acid and cause pH indicator dye to enter its colonies; thus producing a mixture of blue and yellow colors to achieve a shade of green. Other bacteria that do not produce an enzyme to react with the chromogen, but produce acid will have colonies colored by the indicator dye, namely yellow; and other bacteria that neither produce an enzyme that reacts with the substrate nor acid will produce clear colonies in the medium.

Those skilled in the art will devise many other applications for the present invention, and it is therefore intended that the scope of this invention be not limited by the foregoing disclosure, but only by the appended claims.

The invention claimed is:

1. An isolation plating medium for use in processes for the presumptive identification of Shigellae from a sample that also contains other organisms, said plating medium being of a first color prior to inoculation, said medium consisting essentially of at least one carbohydrate of the group consisting of lactose, sucrose, salicin, 2-deoxy-D-ribose, adonitol, dulcitol, inositol, xylose and cellobiose, a pH indicator dye that changes the color of the plating medium to a second color when the pH of the medium changes, at least one chromogenic substrate that reacts to an enzyme to form precipitate in the plating medium of a third color, and an ingredient for thickening the mixture in sufficient quantity to solidify the mixture, whereby microorganisms which do not ferment the carbohydrate and do not produce an enzyme that reacts with a chromogenic substrate will produce colonies in the plating medium of the first color, microorganisms that ferment the carbohydrate but do not produce an enzyme that reacts with a chromogenic substrate will produce colonies in the plating medium of the second color, microorganisms which do not ferment the carbohydrate but do produce an enzyme that reacts with a chromogenic substrate will produce colonies in the plating medium of the third color, and microorganisms that ferment the carbohydrate and produces an enzyme that reacts with a chromogenic substrate will produce colonies in the plating medium of a fourth color that is the color that results from the mixing of the second and third colors, the first, second, third and fourth colors contrasting with each other.

2. An isolation plating medium as set forth in claim 1 wherein the at least one chromogenic substrate in the plating medium is a plurality of chromogenic substrates that react to different enzymes excepting alpha-galactosidase to form precipitate in the plating medium of the third color.

3. An isolation plating medium as set forth in claim 2 wherein the chromogenic substrates comprises a plurality of the members of the group 5-Bromo-4-chloro-3-indoxyl-beta-D-glucopyranoside, 5-Bromo-6-chloro-3-indoxyl-beta-D-glucopyranoside, 3-indoxyl-beta-D-glucopyranoside, 6-chloro-3-indoxyl-beta-D-glucopyranoside, 4-Methylumbelliferyl-beta-D-mannopyranoside, 4-Nitrophenyl-beta-D-mannopyranoside, Methylumbelliferyl-beta-D-xylopyranoside, 2-Nitrophenyl-beta-D-xylopyranoside, 4-Nitrophenyl-beta-D-xylopyranoside, 5-Bromo-4-chloro-3-indoxyl-beta-D-fucopyranoside, 4-Methylumbelliferyl-beta-D-fucopyranoside, 4-Nitrophenyl-beta-D-fucopyranoside, 4-Methylumbelliferyl-beta-D-glucopyranoside, 1-Naphthyl-beta-D-glucopyranoside, 2-Nitrophenyl-beta-D-glucopyranoside, 3-Nitrophenyl-beta-D-glucopyranoside, 4-Nitrophenyl-beta-D-glucopyranoside, 5-Bromo-4-chloro-3-indoxyl-N-acetyl-beta-D-galctosaminide, 6-chloro-3-indoxyl-N-acetyl-beta-D-galactosaminide, 4-Methylumbelliferyl-N-acetyl-beta-D-galctosaminide, and 4-Nitrophenyl-N-acetyl-beta-D-galactosaminide.

4. An isolation plating medium as set forth in claim 3 in combination with an enzyme enhancer.

5. An isolation plating medium as set forth in claim 4 wherein the enzyme enhancer comprises 1-O-Methyl-beta-D-glucopyranoside.

6. An isolation plating medium as set forth in claim 1 in combination with an ingredient providing nutrition for Shigella organisms.

7. An isolation plating medium as set forth in claim 6 wherein the ingredient for providing nutrition for Shigella organisms comprises one or more members of the group casimino acids, dessicated beef extract, yeast extract, and soytone.

8. An isolation plating medium as set forth in claim 1 in combination with an organism inhibitors.

9. An isolation plating medium as set forth in claim 8 wherein the inhibitor comprises one or more members of the group bile salts, bile salts #3, tellurite, cefixime, sodium novobiocin, and cefsulodin.

10. An isolation plating medium for use in processes for the presumptive identification of bacteria from a sample that also contains other organisms, said plating medium being of a first color prior to inoculation and consisting essentially of an ingredient for promoting the growth of the target bacteria, a carbohydrate, a pH indicator dye that changes the color of the plating medium to a second color when the pH of the medium changes, a plurality of chromogenic substrates that react to different enzymes to form precipitate in the plating medium of a third color, and an ingredient for thickening the mixture in sufficient quantity to solidify the mixture, whereby microorganisms which do not ferment the carbohydrate and do not produce an enzyme that reacts with a chromogenic substrate will produce colonies in the plating medium of the first color, microorganisms that ferment the carbohydrate but do not produce an enzyme that reacts with a chromogenic substrate will produce colonies in the plating medium of the second color, microorganisms which do not ferment the carbohydrate but do produce an enzyme that reacts with a chromogenic substrate will produce colonies in the plating medium of the third color, and microorganisms that ferment the carbohydrate and produces an enzyme that reacts with a chromogenic substrate will produce colonies in the plating medium of a fourth color that is the color that results from the mixing of the second and third colors, the first, second, third and fourth colors contrasting with each other.

11. An isolation plating medium for use in processes for the presumptive identification of *Shigella boydii* and *Shigella sonnei* from a sample that also contains other organisms, the plating medium having a first color prior to inoculation, consisting essentially of a nutrient base for promoting the growth of Shigella organisms, one or more inhibitors including an inhibitor for gram positive bacteria, one or more carbohydrates of the group lactose, sucrose, salicin, 2-deoxy-D-ribose, adonitol, dulcitol inositol, xylose and cellobiose, a pH indicator dye that changes the color of the plating medium to a second color when the pH of the medium changes, a chromogenic substrate that reacts to the enzyme alpha-galactosidase to form a precipitate in the plating medium of a third color, and an ingredient for thickening the mixture in sufficient quantity to solidify the mixture, whereby a microorganism which does not ferment the carbohydrate and does not produce alpha-galactosidase enzymes will produce colonies in the plating medium of the first color, a microorganism that ferments the carbohydrate but does not produce alpha-galactosidase enzymes will produce colonies in the plating medium of the second color, *Shigella boydii* and *Shigella sonnei* and other microorganism which do not ferment the carbohydrate but do produce alpha-galactosidase enzymes will produce colonies in the plating medium of the third color, and a microorganism that ferments the carbohydrate and produces alpha-galactosidase enzymes will produce colonies in the plating medium of a fourth color that is the color that results from the mixing of the second and third color, the first, second, third and fourth colors being contrasting colors.

12. An isolation plating medium as set forth in claim 11 wherein the base for promoting the growth of Shigella organisms includes casimino acids, beef extract and yeast extract, bile salts, carbohydrates including lactose, salicin, sucrose, and dulcitol.

13. An isolation plating medium as set forth in claim 11 wherein the chromogenic substrates consist of one or more members of the group 5-Bromo-4-chloro-3-indoxyl-alpha-D-galactopyranoside, 6-chloro-3-indoxyl-alpha-D-galactopyranoside, 4-Methylumbelliferyl-alpha-D-galactopyranoside, 1-Naphthyl-alpha-D-galactopyranoside, 4-Nitrophenyl-alpha-D-galactopyranoside, 4-Methylumbelliferyl-alpha-D-glucopyranoside, 2-Naphthyl-alpha-D-glucopyranoside, 4-Nitrophenyl-alpha-D-glucopyranoside, 5-Bromo-4-chloro-3-indoxyl-alpha-D-glucopyranoside, 5-Bromo-4-chloro-3-indoxyl-alpha-D-mannopyranoside, 2-(6-Bromonaphthyl)-alpha-D-mannopyranoside, 6-chloro-3-indoxyl-alpha-D-mannopyranoside, 4-Methylumbelliferyl-alpha-D-mannopyranoside, 4-Nitrophenyl-alpha-D-mannopyranoside.

14. An isolation plating medium as set forth in claim 13 wherein the enzyme enhancer comprises 1-O-Methyl-be beta-D-glucopyranoside.

15. An isolation plating medium as set forth in claim 1 wherein the chromogenic substrate in the plating medium reacts to alpha-galactosidase enzymes to form precipitate in the plating medium of the third color.

16. An isolation plating medium as set forth in claim 15 wherein the chromogenic substrate comprises a member of the group 5-Bromo-4-chloro-3-indoxyl-alpha-D-galactopyranoside, 6-chloro-3-indoxyl-alpha-D-galactopyranoside, 4-Methylumbelliferyl-alpha-D-galactopyranoside, 1-Naphthyl-alpha-D-galactopyranoside, 4-Nitrophenyl-alpha-D-galactopyranoside, 4-Methylumbelliferyl-alpha-D-glucopyranoside, 2-Naphthyl-alpha-D-glucopyranoside, 4-Nitrophenyl-alpha-D-glucopyranoside, 5-Bromo-4-chloro-3-indoxyl-alpha-D-glucopyranoside, 5-Bromo-4-chloro-3-indoxyl-alpha-D-mannopyranoside, 2-(6-Bromonaphthyl)-alpha-D-mannopyranoside, 6-chloro-3-indoxyl-alpha-D-mannopyranoside, 4-Methylumbelliferyl-alpha-D-mannopyranoside, 4-Nitrophenyl-alpha-D-mannopyranoside.

17. An isolation plating medium as set forth in claim 15 in combination with an enzyme enhancer.

18. An isolation plating medium as set forth in claim 17 wherein the enzyme enhancer comprises one or more members of the group 1-O-Methyl-alpha-D-galactopyranoside, and 1-O-Methyl-alpha-D-mannopyranoside.

19. An isolation plating medium as set forth in claim 1 in combination with an ingredient providing nutrition for Shigella organisms.

20. An isolation plating medium as set forth in claim 19 wherein the ingredient for providing nutrition for Shigella organisms is one or more members of the group casimino acids, dessicated beef extract, yeast extract, and soytone.

21. An isolation plating medium as set forth in claim 1 in combination with an organism inhibitor.

22. An isolation plating medium as set forth in claim 21 wherein the inhibitor comprises one or more members of the group bile salts, bile salts #3, tellurite, cefixime, sodium novobiocin, and cefsulodin.

23. An isolation plating medium for use in processes for the presumptive identification of a target bacteria from a sample that also contains other organisms, said plating medium being of a first color prior to inoculation and consisting essentially of a carbohydrate that is not fermented by the target bacteria, a pH indicator dye that changes the color of the plating medium to a second color when the pH of the medium changes, a plurality of chromogenic substrates that react to the different enzymes produced by the other microorganisms to form precipitate in the plating medium of a third color but do not react to enzymes produced by the target bacteria, and an ingredient for thickening the mixture in sufficient quantity to solidify the mixture, whereby target bacteria which do not ferment the carbohydrate and do not produce an enzyme that reacts with a chromogenic substrate will produce colonies in the plating medium of the first color, microorganisms that ferment the carbohydrate but do not produce an enzyme that reacts with a chromogenic substrate will produce colonies in the plating medium of the second color, microorganisms which do not ferment the carbohydrate but do produce an enzyme that reacts with a chromogenic substrate will produce colonies in the plating medium of the third color, and microorganisms that ferment the carbohydrate and produces an enzyme that reacts with a chromogenic substrate will produce colonies in the plating medium of a fourth color that is the color that results from the mixing of the second and third colors, the first, second, third and fourth colors contrasting with each other.

* * * * *